US00PP30229P2

(12) United States Plant Patent
Bradford et al.

(10) Patent No.: US PP30,229 P2
(45) Date of Patent: Feb. 26, 2019

(54) CHERRY TREE NAMED 'GLENSWEET II'

(50) Latin Name: *Prunus avium*
Varietal Denomination: Glensweet II

(71) Applicants: Lowell Glen Bradford, Le Grand, CA (US); Jon M. Quisenberry, Le Grand, CA (US)

(72) Inventors: Lowell Glen Bradford, Le Grand, CA (US); Jon M. Quisenberry, Le Grand, CA (US)

( * ) Notice: Subject to any disclaimer, the term of this patent is extended or adjusted under 35 U.S.C. 154(b) by 0 days.

(21) Appl. No.: 15/732,743

(22) Filed: Dec. 26, 2017

(51) Int. Cl.
*A01H 5/08* (2018.01)

(52) U.S. Cl.
USPC ..... Plt./181

(58) Field of Classification Search
USPC ..... Plt./181

CPC ..... A01H 5/08; A01H 5/085; A01H 5/0837; A01H 5/0216; A01H 6/7445
See application file for complete search history.

(56) References Cited

U.S. PATENT DOCUMENTS

PP12,859 P2 8/2002 Bradford
PP27,369 P3 11/2016 Bradford

*Primary Examiner* — June Hwu

(57) ABSTRACT

The present invention relates to a cherry tree, *Prunus avium*, and more particularly to a new and distinct variety broadly characterized by a medium size, vigorous, hardy, self-unfruitful, and productive tree. The fruit matures under the ecological conditions described in early to mid May, with first picking on May 9, 2017. The fruit is uniformly large in size, sweet and sub-acidic in flavor, oblate in shape, semi-freestone in type, firm in texture, mostly yellow in flesh color, and red and yellow in skin color. The stem is long and is strongly attached to the fruit.

1 Drawing Sheet

Botanical classification: *Prunus avium.*
Varietal denomination: 'GLENSWEET II'.

BACKGROUND OF THE VARIETY

In a continuing effort to improve the quality of shipping fruits, we, the inventors, typically hybridize a large number of peach, nectarine, plum, apricot, and cherry seedlings each year. We also grow a smaller number of open pollinated seeds of each of these fruits, usually to capture recessive traits. The present invention relates to a new and distinct variety of cherry tree, which has been denominated varietally as 'Glensweet II'.

During a typical blooming season we isolate as seed parents individual cherry trees by covering them with screen houses. A hive of bees is placed inside each such house, and bouquets to provide pollen from different cherry trees are placed in buckets near the trees approximately every two days for the duration of the bloom. During 2001 one such house containing 'Glenred' (U.S. Plant Pat. No. 12,859) cherry tree was crossed by us in this manner. To pollinate this cherry, we selected bouquets from several sources of cherry trees without keeping specific written details. Upon reaching maturity the fruit from this cherry tree was harvested and the seeds were removed, cracked, stratified, and germinated as a group with the label 'Cherry House'. They were grown as seedlings on their own root in our greenhouse, and upon reaching dormancy transplanted to a cultivated area of our experimental orchard located near Le Grand, Calif. in Merced County (San Joaquin Valley). During the summer of 2007 the claimed variety was selected by us as a single tree from the group of seedlings described above. Subsequent to origination of the present variety of cherry tree, we asexually reproduced it by budding and grafting in the experimental orchard described above, and such reproductions were true to the original tree in all respects. The reproduction of the variety included the use of 'Colt' (U.S. Plant Pat. No. 4,059) rootstock, upon which the present variety was compatible and true to type.

The present variety is similar to its seed parent, 'Glenred' (U.S. Plant Pat. No. 12,859) cherry, by blooming densely in the early season, by being self-unfruitful, by having oval to reniform leaf glands, by being productive, and by producing cherries that have a long stem and that are semi-freestone in type, firm in texture, oblate in shape, and fairly crack resistant, but is distinguished therefrom by producing cherries that ripen about three days earlier, that are larger in size, that are yellow instead of red in flesh color, that are a red and yellow two-tone instead of full red in skin color, that are sub-acidic and sweeter in flavor, and that have a stem that is more firmly attached to the fruit.

The present variety is most similar to 'Glencrest' (U.S. Plant Pat. No. 27,369) cherry, by being a medium size and moderately vigorous tree, by having a heavy bloom, by being self-unfruitful, by having oval to reniform leaf glands, by being productive, and by producing cherries that have a strongly attached stem and that are somewhat freestone in type, firm in texture, oblate in shape, and fairly crack resistant, but is distinguished therefrom by blooming about four days earlier and by producing cherries that ripen about five days earlier, that are larger in size, that are yellow instead of red in flesh color, that are a red and yellow two-tone instead of full red in skin color, that are sub-acidic and sweeter in flavor, and that have a much longer stem.

SUMMARY OF VARIETY

In summary, the present cherry variety is characterized by a medium size, vigorous, hardy, self-unfruitful, and productive tree. The fruit matures under the ecological conditions described in early to mid May, with first picking on May 9, 2017. The fruit is uniformly large in size, sweet and subacidic in flavor, oblate in shape, semi-freestone in type, firm in texture, mostly yellow in flesh color, and red and yellow in skin color. The stem is long and is strongly attached to the fruit.

DRAWING

The accompanying photograph displays five whole fruits with the stems attached, two whole fruits detached from the stems to exhibit the skin color and form, one divided fruit to reveal the flesh, fibers, and stone, two insets depicting flowers and buds, a typical tip shoot, and several leaves, all typical of the subject variety.

POMOLOGICAL CHARACTERISTICS

Referring now more specifically to the pomological characteristics of this new and distinct variety of cherry tree, the following has been observed under the ecological conditions prevailing near Le Grand, Merced County (San Joaquin Valley), Calif., and was developed at the state of firm ripe on May 18, 2017, on a multiplied tree using 'Colt' (U.S. Plant Pat. No. 4,059) rootstock during its eighth growing season. All major color code designations are by reference to the Inter-Society Color Council, National Bureau of Standards. Common color names are also used occasionally.

PARENTAGE

Seed parent: 'Glenred' cherry (U.S. Plant Pat. No. 12,859).
Pollen parent: Unknown.

TREE

Size: Medium, maintained to a height of 9' [2.74 m.] and a spread of 7' [2.13 m.] after eight growing seasons utilizing typical pruning.

Vigor: Vigorous, responding typically to irrigation and fertilization. The plant should be grown on a standard commercial rootstock for production purposes.

Growth: Spreading and dense.

Form: Pruned to a vase shape.

Hardiness: Hardy with respect to central California winters.

Heat tolerance: Observed to perform adequately in typical central California climatic conditions, which typically include extended periods of heat.

Drought tolerance: Variety is developed for commercial orchards and requires regular irrigation.

Production: Productive.

Fertility: Self-unfruitful, must be cross pollinated by another early to mid seasonal blooming cherry variety, such as 'Sweet Fruitful' (U.S. Plant Pat. No. 21,926).

Bearing: Fairly regular bearer, dependent upon seasonal blooming weather.

Leaf bud burst: Toward the end of flowering.

Trunk:

*Size*.—Stocky to medium, reaching a maximum diameter of 4" [101.6 mm.] after the eighth growing season.

*Texture*.—Smooth to medium roughness.

*Bark color*.—A Light grayish brown [60. l.gy.Br] and Light brown [57. l.Br] variegation with Dark grayish brown [62. d.gy.Br] crevices present.

*Lenticels*.—Approximate Number Per Square Inch: 6. Color: Brownish gray [64. brGy]. Average Size: Length is 7/16" [11.1 mm.] with a width of 1/8" [3.2 mm.]. Shape: Eye-shaped, elongated.

Branches:

*Size*.—Medium, diameter of main scaffold measured 12" above the crotch is 3" [76.2 mm.], diameter of limb measured 12" above first fork is 2" [50.8 mm.].

*Texture*.—Smooth to medium on first and second year wood, increasing roughness with age.

*Color*.—1st Year Wood topside: Grayish red [19. gy.R]. 1st Year Wood underside: Brilliant yellow green [116. brill.YG]. 2nd Year Wood: A Light grayish brown [60. l.gy.Br] and Brownish gray [64. brGy] variegation with Grayish brown [61. gy.Br] crevices present.

*Lenticels*.—Number Per Square Inch: About 40 on second year wood. Color: Deep yellowish brown [75. deep yBr]. Average Size: Length is 1/8" [3.2 mm.] and width is 1/32" [0.8 mm.]. Shape: Eye-shaped, elongated.

Leaves:

*Size*.—Medium. Average Length: 5" [127 mm.]. Average Width: 2 1/16" [52.4 mm.].

*Arrangement*.—Alternate.

*Thickness*.—Medium.

*Form*.—Elliptical.

*Apex*.—Acuminate.

*Base*.—Acute to rounded.

*Surface*.—Smooth on both sides.

*Color*.—Dorsal Surface: Moderate olive green [125. m.OlG]. Ventral Surface: Moderate yellow green [120. m.YG].

*Red midvein*.—Absent.

*Margin*.—Finely serrate.

*Venation*.—Pinnately net veined.

*Vein color*.—Light yellow green [119. l.YG].

*Petiole*.—Average Length: 1 3/8" [34.9 mm.]. Average Thickness: 1/16" [1.6 mm.]. Color: Dark purplish red [259. d.pR] on the topside, Brilliant yellow green [116. brill.YG] underneath.

*Stipules*.—Number: 2 per leaf, up to 6 per growing tip. Average Length: 5/16" [7.9 mm.]. Color: Brilliant yellow green [116. brill.YG] toward the apex, Pale yellow green [121. p.YG] toward the base.

*Glands*.—Number: Usually 2 per leaf. Position: Usually alternate. Size: Medium, 1/48" [0.5 mm.] in diameter. Form: Oval to reniform. Color: Brilliant yellow green [116. brill.YG] with a Deep reddish brown [41. deep rBr] center.

*Leaf buds*.—Pointed.

Flower buds:

*Hardiness*.—Hardy with respect to central California blooming season.

*Diameter*.—Typically 5/16" [7.9 mm.] 3 days before bloom.

*Length*.—Typically 5/8" [15.9 mm.] 3 days before bloom.

*Form*.—Not appressed.

*Surface*.—Non-pubescent.

*Tip color*.—Pinkish white [9. pkWhite].

Flowers: Perfect, complete, perigynous, usually a single pistil, typically about twenty stamens, five sepals and petal locations alternately positioned.

*Average flower diameter*.—1 3/4" [44.5 mm.].

*Average flower depth.*—½" [12.7 mm.] when fully open.
*Average pedicel length.*—⅜" [9.5 mm.].
*Number of petals.*—Usually five, no extra petals or fragments observed.
*Petal arrangement.*—Overlapping.
*Petal shape.*—Oval.
*Petal margin.*—Somewhat wavy with a few notches present.
*Average petal diameter.*—⅝" [15.9 mm.].
*Average petal length.*—11/16" [17.5 mm.].
*Petal apex.*—Rounded.
*Petal base.*—Rounded to slightly cuneate.
*Petal color.*—White [263. White] on both sides.
*Anther color.*—Brilliant yellow [83. brill.Y].
*Stigma color.*—Brilliant greenish yellow [98. brill.gY].
*Stigma position.*—Typically located about 3/16" [4.8 mm.] above the nearby anthers.
*Stamen position.*—Typically located about 1/32" [0.8 mm.] below the petals.
*Ovary.*—Non-pubescent.
*Sepal color.*—Grayish purplish red [262. gy.pR] over Deep greenish yellow [100. deep gY] on the outer surface. The inner surface is Pale yellow green [121. p.YG].
*Sepal outer surface.*—Slightly pubescent.
*Sepal length.*—⅜" [9.5 mm.].
*Sepal width.*—3/16" [4.8 mm.].
*Sepal apex.*—Rounded to slightly acute.
*Sepal margin.*—Fairly smooth.
*Average pistil length.*—13/16" [20.6 mm.].
*Average stamen length.*—9/16" [14.3 mm.].
*Fragrance.*—Moderate.
*Pollen production.*—Moderate.
*Pollen color.*—Strong yellow [84. s.Y].
*Bloom density.*—Heavy.
*Blooming period.*—Early, blooms two days before 'Glenred' (U.S. Plant Pat. No. 12,859) cherry.
*Onset of bloom.*—One percent on Mar. 7, 2017.
*Date of full bloom.*—Mar. 17, 2017.
*Duration of bloom.*—One to two weeks, dependent on ambient temperature.
*Number per cluster.*—Usually 2 to 6, 3 average.

FRUIT

Maturity when described: Firm ripe, May 18, 2017.
Date of first picking: May 9, 2017.
Date of last picking: May 19, 2017.
Size: Uniform, large.
*Average diameter axially.*—1¼" [31.8 mm.].
*Average diameter across cheek plane.*—1 5/16" [33.3 mm.].
*Average diameter across suture plane.*—1 1/16" [27.0 mm.].
*Typical weight.*—0.51 ounces [14.6 grams].
Form: Uniform, symmetrical, somewhat oblate.
*Axial view form.*—Elliptical to oblate.
*Suture plane form.*—Oval.
*Cheek plane form.*—Oblate.
Suture: An intermittent Moderate red [15. m.R] line located in a very shallow trough, extending from the stem cavity just to the apex.
Ventral surface: Rounded slightly, lipped on both sides.
Lips: Equal.
Cavity: Flaring, rounded, suture showing on one side.
*Depth.*—⅛" [3.2 mm.].
*Breadth.*—7/16" [11.1 mm.].
Base: Truncate, moderately cordate if viewed parallel to the suture.
Apex: Rounded.
Pistil point: A Grayish yellow [90. gy.Y] dot.
Stem: Moderately long.
*Average length.*—1 15/16" [49.2 mm.].
*Average width.*—1/16" [1.6 mm.].
*Attachment.*—Very strong.
Skin:
*Thickness.*—Medium.
*Surface.*—Smooth.
*Tenacity.*—Tenacious to the flesh.
*Astringency.*—Very slight.
*Tendency to crack.*—None observed in dry season.
*Color.*—A Deep red [13. deep R] over Brilliant yellow [83. brill.Y] background with some Vivid red [11. v.R] freckling in the transitional areas.
*Lenticels.*—Number Per Square Inch: About 60 toward the apex. Average diameter: 1/64" [0.4 mm.].
Flesh:
*Color.*—Pale yellow [89. p.Y] with very slight Moderate pink [5. m.Pk] bleeding very close to the skin and Yellowish white [92. yWhite] fibers throughout.
*Surface of pit cavity.*—Covered with Yellowish white [92. yWhite] fibers.
*Amygdalin.*—Moderate.
*Juice.*—Abundant, rich.
*Juice color.*—Pale pink [7. p.Pk].
*Texture.*—Firm, crisp.
*Fibers.*—Abundant, fine, tender.
*Ripens.*—Fairly even, slightly earlier on the shoulders.
*Flavor.*—Sub-acidic, very sweet, typically 24 brix.
*Aroma.*—Very slight.
*Eating quality.*—Excellent.

STONE

Type: Semi-freestone.
Form: Oval.
Hilum: Narrow, oval.
Base: Rounded.
Apex: Rounded.
Sides: Mostly equal.
Surface: Fairly smooth.
External color of stone: Light olive brown [94. l.OlBr].
Pit wall color when cracked: Light yellowish brown [76. l.yBr].
Cavity surface color: Moderate yellowish brown [77. m.yBr].
Average pit wall thickness: 1/16" [1.6 mm.].
Average width: ⅜" [9.5 mm.].
Average length: 7/16" [11.1 mm.].
Average breadth: ¼" [6.4 mm.].
Tendency to split: None observed.
Kernel:
*Form.*—Oval.
*Skin color.*—Yellowish white [92. yWhite] when first removed.
*Pellicle color.*—Dark olive brown [96. d.OlBr].
*Vein color.*—None observed.
*Taste.*—Bitter.
*Viable.*—Yes.

*Average width.*—¼" [6.4 mm.].
*Average length.*—5/16" [7.9 mm.].
*Amygdalin.*—Moderate.

USE

Market: Fresh market and long distance shipping.
Keeping quality: Good, fruit quality observed to remain in good condition after 21 days in standard cold room at 36° Fahrenheit [2° Celsius].
Shipping quality: Good.
Resistance to insects: Not tested.
Resistance to diseases: Not tested.

OTHER NOTES

Although the new variety of cherry tree possesses the described characteristics under the ecological conditions at Le Grand, Calif., in the central part of the San Joaquin Valley, it is to be expected that variations in these characteristics may occur when farmed in areas with different climatic conditions, different soil types, and/or varying cultural practices.

We claim:

1. A new and distinct variety of cherry tree, substantially as illustrated and described, that is most similar to 'Glencrest' (U.S. Plant Pat. No. 27,369) cherry, by being a medium size and moderately vigorous tree, by having a heavy bloom, by being self-unfruitful, by having oval to reniform leaf glands, by being productive, and by producing cherries that have a strongly attached stem and that are somewhat freestone in type, firm in texture, oblate in shape, and fairly crack resistant, but is distinguished therefrom by blooming about four days earlier and by producing cherries that ripen about five days earlier, that are larger in size, that are yellow instead of red in flesh color, that are a red and yellow two-tone instead of full red in skin color, that are sub-acidic and sweeter in flavor, and that have a much longer stem.

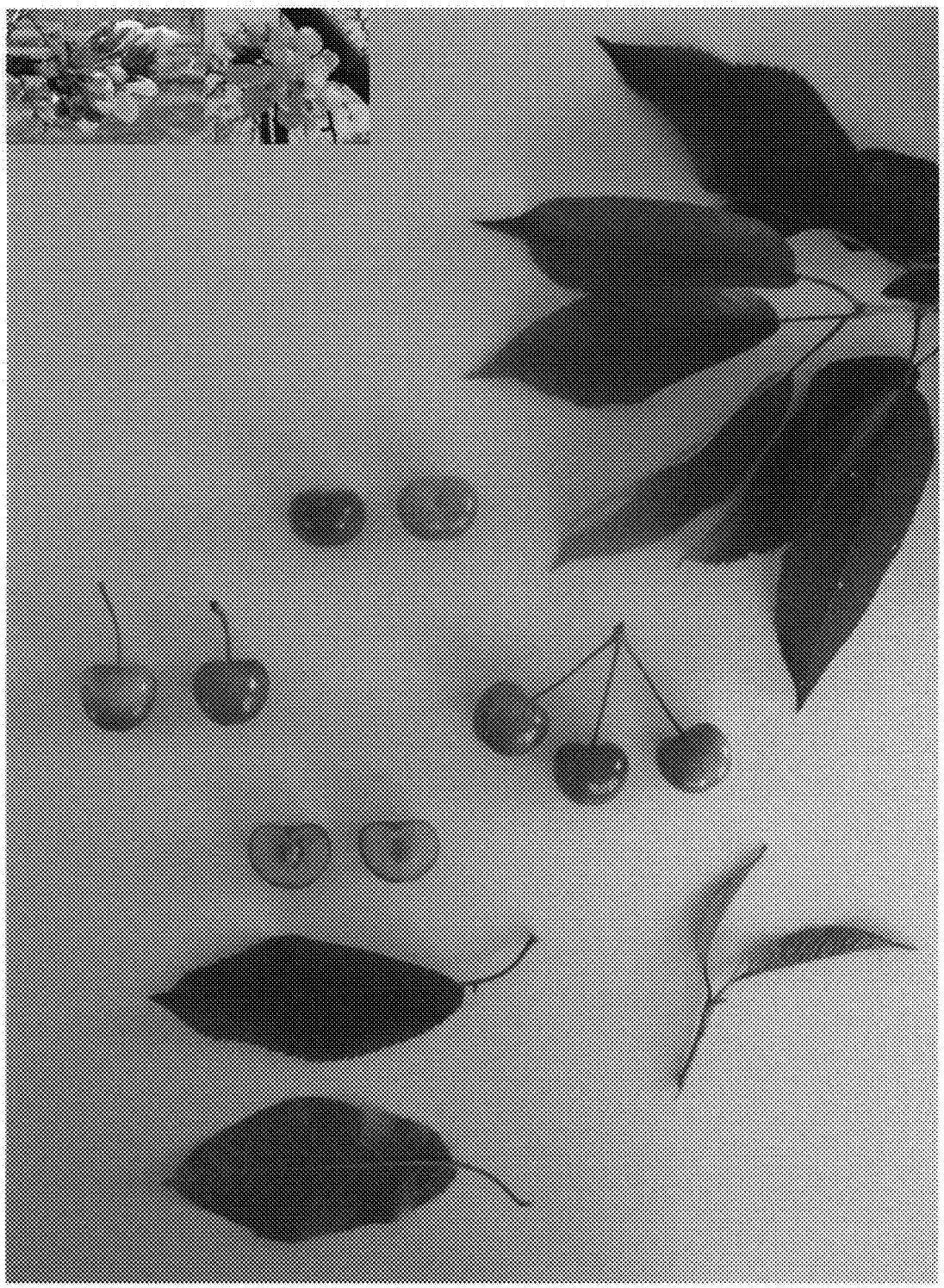

* * * * *